(12) United States Patent
Heinrich

(10) Patent No.: US 7,311,661 B2
(45) Date of Patent: Dec. 25, 2007

(54) ORGAN RETRACTOR AND METHOD OF USING THE SAME

(75) Inventor: Russell Heinrich, Hamden, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 144 days.

(21) Appl. No.: 10/512,597

(22) PCT Filed: May 9, 2003

(86) PCT No.: PCT/US03/14774

§ 371 (c)(1),
(2), (4) Date: Oct. 21, 2004

(87) PCT Pub. No.: WO03/094754

PCT Pub. Date: Nov. 20, 2003

(65) Prior Publication Data

US 2005/0165280 A1 Jul. 28, 2005

Related U.S. Application Data

(60) Provisional application No. 60/379,378, filed on May 9, 2002.

(51) Int. Cl.
*A61B 17/02* (2006.01)
(52) U.S. Cl. .......................... 600/206; 600/210; 600/37
(58) Field of Classification Search ................ 600/37, 600/203, 204, 206, 208–210, 215; 606/113, 606/200
See application file for complete search history.

(56) References Cited

U.S. PATENT DOCUMENTS

| | | |
|---|---|---|
| 3,831,587 A | 8/1974 | Boyd |
| 3,857,386 A | 12/1974 | Ashbell |
| 4,190,042 A | 2/1980 | Sinnreich |
| 4,198,960 A | 4/1980 | Utsugi |
| 4,744,363 A | 5/1988 | Hasson |
| 4,950,283 A | 8/1990 | Dzubow et al. |
| 5,074,840 A | 12/1991 | Yoon |
| 5,150,706 A | 9/1992 | Cox et al. |
| 5,176,128 A | 1/1993 | Andrese |
| 5,178,133 A | 1/1993 | Pena |
| 5,195,505 A | 3/1993 | Josefsen |
| 5,245,987 A | 9/1993 | Redmond et al. |
| 5,250,056 A | 10/1993 | Hasson |
| 5,261,917 A | 11/1993 | Hasson et al. |
| 5,267,554 A | 12/1993 | Wilk |
| 5,271,385 A | 12/1993 | Bailey |

(Continued)

FOREIGN PATENT DOCUMENTS

DE 35 22 649 1/1986

(Continued)

*Primary Examiner*—Cary E. O'Connor

(57) ABSTRACT

The present disclosure relates to an endoscopic retractor apparatus for retracting and/or positioning organs during minimally invasive surgery. The apparatus includes an elongate shaft having proximal and distal ends and a lumen extending therebetween, and a retracting sleeve operatively associated with the elongate shaft. The retracting sleeve includes a first and a second spindle each disposable in the lumen of the elongated shaft, each spindle being selectively translatable through the lumen of the elongate shaft, and a sling portion extending between the distal ends of the first and second spindles, the sling portion defining a cradle for receiving organs therein, the sling portion being selectively movable upon translation of at least one of the first and second spindles.

26 Claims, 3 Drawing Sheets

U.S. PATENT DOCUMENTS

| | | | |
|---|---|---|---|
| 5,281,237 A | 1/1994 | Gimpelson | |
| 5,301,658 A | 4/1994 | Zhu et al. | |
| 5,318,013 A | 6/1994 | Wilk | |
| 5,337,736 A | 8/1994 | Reddy | |
| 5,350,391 A | 9/1994 | Iacovelli | |
| 5,359,995 A | 11/1994 | Sewell, Jr. | |
| 5,362,294 A | 11/1994 | Seitzinger | |
| 5,374,261 A | 12/1994 | Yoon | |
| 5,391,180 A | 2/1995 | Tovey et al. | |
| 5,403,329 A | 4/1995 | Hinchcliffe | |
| 5,456,695 A | 10/1995 | Herve Dallemagne | |
| 5,470,338 A | 11/1995 | Whitfield et al. | |
| 5,474,568 A | 12/1995 | Scott | |
| 5,486,182 A * | 1/1996 | Nakao et al. | 606/114 |
| 5,501,653 A | 3/1996 | Chin | |
| 5,507,796 A | 4/1996 | Hasson | |
| 5,549,627 A | 8/1996 | Kieturakis | |
| 5,549,636 A | 8/1996 | Li | |
| 5,582,577 A | 12/1996 | Lund et al. | |
| 5,593,443 A | 1/1997 | Carter et al. | |
| 5,613,939 A | 3/1997 | Failla | |
| 5,647,836 A | 7/1997 | Blake, III et al. | |
| 5,656,012 A | 8/1997 | Sienkiewicz | |
| 5,662,676 A | 9/1997 | Koninckx | |
| 5,735,289 A | 4/1998 | Pfeffer et al. | |
| 5,735,845 A | 4/1998 | Zupkas | |
| 5,746,763 A | 5/1998 | Benderev et al. | |
| 5,775,661 A | 7/1998 | Matsumoto et al. | |
| 5,792,042 A | 8/1998 | Cohen et al. | |
| 5,810,721 A | 9/1998 | Mueller et al. | |
| 5,817,973 A | 10/1998 | Elco | |
| 5,860,987 A | 1/1999 | Ratcliff et al. | |
| 5,891,162 A | 4/1999 | Sugarbaker et al. | |
| 5,895,352 A * | 4/1999 | Kleiner | 600/206 |
| 5,904,646 A | 5/1999 | Jarvik | |
| 5,904,711 A | 5/1999 | Flom et al. | |
| 5,954,057 A | 9/1999 | Li | |
| 5,968,074 A | 10/1999 | Prestel | |
| 5,993,384 A * | 11/1999 | Lunsford et al. | 600/209 |
| 5,993,461 A | 11/1999 | Abae | |
| 6,010,447 A | 1/2000 | Kardjian | |
| 6,015,382 A * | 1/2000 | Zwart et al. | 600/207 |
| 6,027,519 A | 2/2000 | Stanford | |
| 6,039,686 A | 3/2000 | Kovac | |
| 6,042,534 A | 3/2000 | Gellman et al. | |
| 6,042,536 A | 3/2000 | Tihon et al. | |
| 6,048,309 A | 4/2000 | Flom et al. | |
| 6,068,591 A | 5/2000 | Bruckner et al. | |
| 6,077,214 A | 6/2000 | Mortier et al. | |
| 6,090,041 A | 7/2000 | Clark et al. | |
| 6,090,043 A | 7/2000 | Austin et al. | |
| 6,110,101 A | 8/2000 | Tihon et al. | |
| 6,117,067 A | 9/2000 | Gil-Vernet | |
| 6,142,935 A | 11/2000 | Flom et al. | |
| 6,165,120 A | 12/2000 | Schweich, Jr. et al. | |
| 6,165,121 A | 12/2000 | Alferness | |
| 6,165,122 A | 12/2000 | Alferness | |
| 6,206,827 B1 | 3/2001 | Chin et al. | |
| 6,206,889 B1 | 3/2001 | Bennardo | |
| 6,221,005 B1 | 4/2001 | Bruckner et al. | |
| 6,245,082 B1 | 6/2001 | Gellman et al. | |
| 6,248,088 B1 | 6/2001 | Yoon | |
| 2001/0000533 A1 | 4/2001 | Kovac | |

FOREIGN PATENT DOCUMENTS

| | | |
|---|---|---|
| DE | 35 42 667 | 6/1986 |
| WO | WO 01/35831 | 5/2001 |
| WO | WO 03/094744 | 11/2003 |

* cited by examiner

ORGAN RETRACTOR AND METHOD OF USING THE SAME

CROSS-REFERENCE TO RELATED APPLICATIONS

This is a National Stage Application of PCT/US 03/14774 under 35 USC §371(a), which claims the benefit of and priority to U.S. Provisional Patent Application Ser. No. 60/379,378, filed May 9, 2002, the entire contents of which are hereby incorporated by reference.

BACKGROUND

1. Technical Field

The present disclosure relates to devices and methods used for retracting organs during surgical procedures and, more particularly, to an endoscopic apparatus for retracting or positioning organs during minimally invasive surgery.

2. Background of Related Art

As a result of the recent technological improvements in surgical instruments, surgical procedures, using minimally invasive techniques, are routinely performed which surgical procedures cause less trauma to the patient. Some minimally invasive surgical procedures have limitations due to the small internal diameter of many commonly used cannulas and trocar systems. As a result, instrument manufacturers must come up with innovative and novel solutions for using many common instruments such as organ retractors and tissue retrieval bags which utilize deformable frame openings to fit through the trocar and into the patient. In fact, some organ retractors and tissue retrieval bags use inflatable frames which form components used for manipulating tissue. An exemplary inflatable organ retraction device is disclosed in U.S. Pat. No. 5,823,945 to Moll, et al., the entire content of which is incorporated herein by reference.

As a result thereof, additional systems for pressurizing the inflatable frames are needed. As can be appreciated, inflatable tissue retrieval instruments tend to be vulnerable to accidental deflation in the operating theater and are unnecessarily dependent upon the rigidity of the inflatable structure to support the organ and/or contain the tissue as it is manipulated. Moreover, inflatable type instruments tend to be more complex and costly than corresponding non-inflatable instruments.

A continuing need exists for an endoscopic apparatus for retracting an organ that reduces the forces exerted on the organs and enables improved control of the organ.

SUMMARY

The present disclosure relates to an endoscopic retractor apparatus for retracting an organ during minimally invasive surgery. The apparatus includes an elongate shaft having proximal and distal ends and a lumen extending therebetween, and a retracting sleeve operatively associated with the elongate shaft. The retracting sleeve includes a first and a second spindle each disposable in the lumen of the elongated shaft, each spindle being selectively translatable through the lumen of the elongate shaft, and a sling portion extending between the distal ends of the first and second spindles, the sling portion defining a cradle for receiving organs therein, the sling portion being selectively movable upon translation of at least one of the first and second spindles.

In certain preferred embodiments, the first spindle and the second spindle are integrally formed with the sling portion.

In certain embodiments, the endoscopic retractor apparatus further includes a control portion operatively connected to a proximal end of each of the shaft, the first spindle and the second spindle. The control portion cooperates with the first and the second spindles to allow a user to remotely move the sling portions to engage the organs.

The control portion desirably includes a locking mechanism for maintaining the sling portion in a desired position relative to the retracting sleeve. The locking mechanism maintains the sling portion in at least one of a deployed and a retracted position.

The endoscopic retractor apparatus preferably includes a first position in which the sling portion of the retraction sleeve is at least partially retained in the lumen of the elongate shaft and a second position in which the sling portion of the retraction sleeve is not retained in the lumen of the elongated shaft. When the apparatus is in the second position the sling portion desirably defines a cradling area for engaging the organs.

Preferably, the cradling area is in the form of an open loop. It is contemplated that the sling portion is fabricated from a material which reduces the incidents of ischemia to the organs when in contact therewith, such as, for example, mesh, ribbon and/or cloth. The sling portion may include ribbing provided along a tissue contacting surface thereof for enhancing a gripping force between the sling portion and the organs.

In certain embodiments, the sling portion includes a plurality of ports formed along a tissue contacting surface thereof. The sling portion can be operatively connected to a control portion, wherein the control portion is configured and adapted to deliver a vacuum to at least a portion of the plurality of ports formed in the sling portion. The vacuum can be delivered to the portion of the plurality of ports through at least one of the first and second spindles.

In certain embodiments, the endoscopic retractor apparatus further includes a cinch configured and adapted to constrict at least a portion of the sling portion about the organs. The cinch is a substantially rigid annular structure. The cinch can be disposed about the first and the second spindle. Accordingly, as the cinch is displaced in a direction to space the cinch from the distal end of the first and the second spindles, the sling portion is constricted.

In another embodiment, it is envisioned that endoscopic retractor apparatus further includes a cinching mechanism configured and adapted to constrict at least a portion of the sling portion about the organs. The cinching mechanism includes an elongate tubular body translatably received in the lumen of the elongate shaft, and a loop extending from a distal end of the elongate tubular body, the loop defining an opening, wherein the opening of the loop can be enlarged by releasing loop from the tubular body and the opening of the loop can be reduced by withdrawing loop into the tubular body. The loop can be fabricated from at least one of sutures and wires. Accordingly, when the loop of the cinching mechanism is positioned between the sling portion and the distal ends of the spindles, when the organs are contained within the sling portion, withdrawal of loop into tubular body causes the sling portion to constrict around the organs.

In certain embodiments, the elongate shaft includes a first section defining a lumen extending therethrough, wherein the first spindle is disposable in the lumen of the first section and is selectively translatable therethrough, and a second section defining a lumen extending therethrough, wherein the second spindle is disposable in the lumen of the second section and is selectively translatable therethrough.

The first and second sections of the elongate shaft have a first position in which the first and second sections are in vertical registration with one another and a second position in which the first and second sections are out of vertical alignment with one another. It is envisioned that the first section is pivotably attached to the second section. Accordingly, when the first and second sections are moved from the first position to the second position, the sling portion is opened, and when the first and second sections are moved from the second position to the first position, the sling portion is closed.

Each of the first and second sections may be fabricated from a shape memory alloy. Accordingly, the elongate shaft has a first configuration in which distal ends of the first and second sections are in vertical registration with one another and a second configuration in which the distal ends of the first and second sections are transversely separated from one another after introduction to a body cavity. In certain embodiments, the first and second sections are biased toward the second configuration. The endoscopic retractor apparatus further includes a sleeve disposable about the tubular shaft, wherein the elongate shaft is urged from the second configuration to the first configuration upon withdrawal of the tubular shaft through the sleeve.

The presently disclosed endoscopic organ retractor, together with attendant advantages, will be best understood by reference to the following detailed description in conjunction with the figures below.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Figure 1:
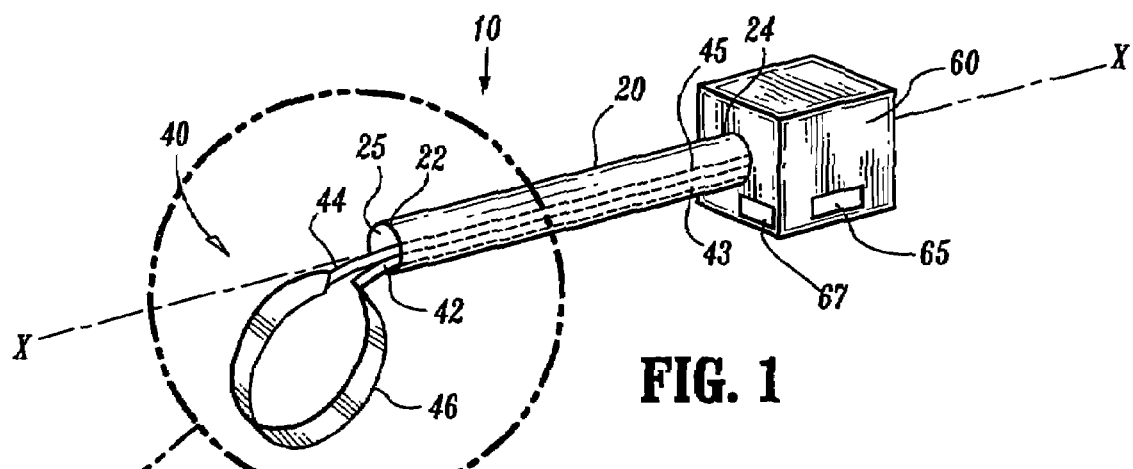
FIG. 1 is a perspective view of an endoscopic retractor apparatus in accordance with an embodiment of the present invention.

Preferred embodiments of the presently disclosed organ retractors will now be described in detail with reference to the drawing figures wherein like reference numerals identify similar or identical elements. In the drawings and in the description which follows, the term "proximal", as is traditional, will refer to the end of the surgical device or instrument of the present disclosure which is closest to the operator, while the term "distal" will refer to the end of the device or instrument which is furthest from the operator.

Figure 2:
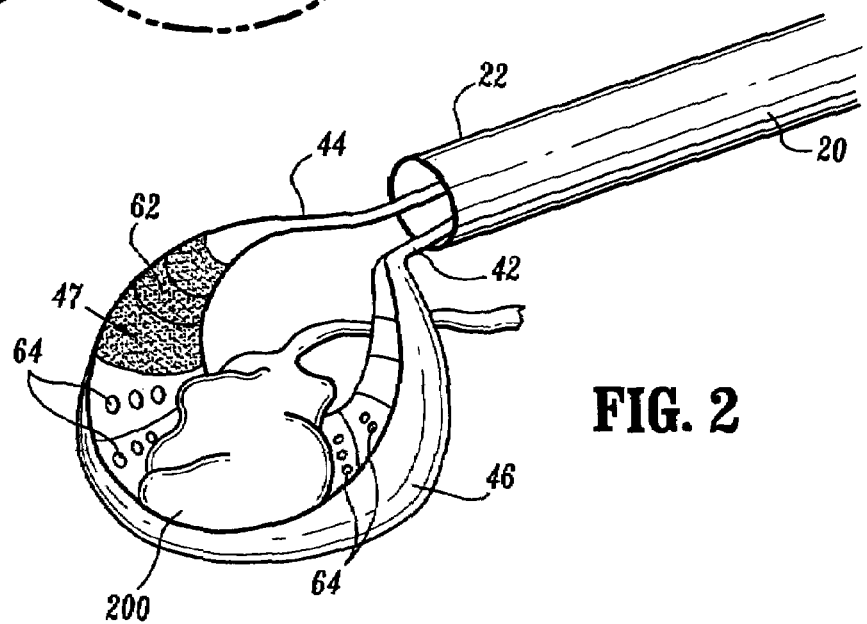
FIG. 2 is an enlarged perspective view of an endoscopic retractor apparatus in accordance with the embodiment of FIG. 1.
Figure 3:
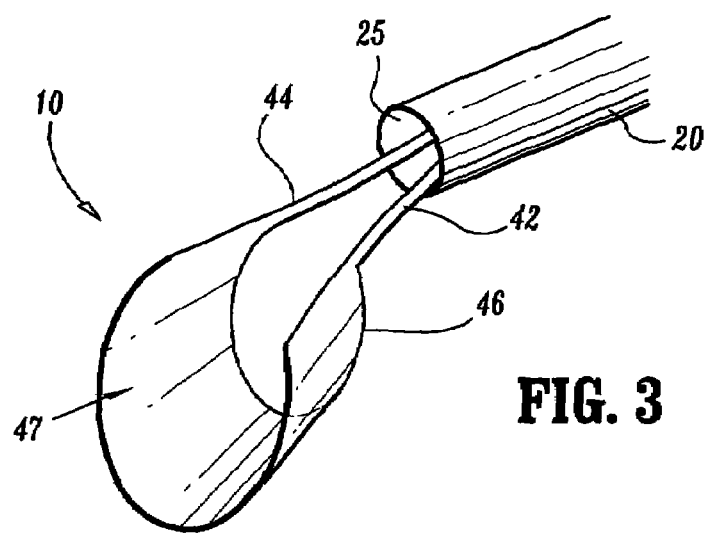
FIG. 3 is an enlarged perspective view of an endoscopic retractor apparatus in accordance with the embodiment of FIGS. 1-2 of the area indicated "3" of FIG. 1.

Referring now to FIGS. 1-3, an andoscopic retractor apparatus, in accordance with the principles of the present disclosure, is shown generally as reference numeral 10. Retractor 10 is desirably configured and adapted to retract organs, such as, for example, the liver, the intestines, the uterus or the lungs during minimally invasive surgery. Retractor 10 is preferably designed for use with an endoscope and is selectively configurable to retract or manipulate organs and tissue within an operating cavity. Retractor 10 includes a tubular shaft 20, a ribbon-like retracting sleeve or sling 40 receivable in tubular shaft 20. The retractor desirably includes a control portion 60 operatively associated with tubular shaft 20 and retracting sleeve 40.

Tubular shaft 20 includes a distal end 22 and a proximal end 24 and defines a lumen 25 therebetween. The tubular shaft 20 shown has a generally circular cross-sectional shape, but the tubular shaft 20 may have any shape. It is envisioned that tubular shaft 20 is fabricated from a generally rigid or relatively rigid material. As seen in FIG. 1, proximal end 24 is connected to control portion 60 which enables the surgeon to selectively manipulate shaft 20 as needed during surgery.

Retracting sleeve 40 preferably includes a pair of elongate spindles 42 and 44 having an elongate flexible material in the form of a sling portion 46 extending between the distal ends of spindles 42 and 44. As will be described in greater detail below, when retracting sleeve 40 is in a deployed position (i.e., sling portion 46 is extended out of distal end 22 of tubular shaft 20) sling portion 46 defines a cradling area 47 (see FIG. 3) which extends between the distal ends of spindles 42 and 44. Spindles 42 and 44 include proximal portions 43 and 45 which allow a user to remotely manipulate sling portion 46 to retract an organ 200 (see FIG. 2). In particular, spindles 42 and 44 may be constructed from rods, sutures, or wires which attach to control portion 60 and allow the user to remotely orient sling portion 46 about organ 200. More particularly, spindles 42 and 44 are constructed from a material suitable for sliding within tubular shaft 20. In certain embodiments, the spindles are formed integrally with the sling portion 46. Preferably, sling portion 46 is configured and adapted to gently support organ 200 during retraction. Sling portion 46 is desirably fabricated from a mesh, ribbon or other cloth type material, or a combination of materials, preferably having properties for reducing the incidents of ischemia to organ 200 during its retraction. Sling portion 46, spindles 42 and 44, and shaft 20 are desirably formed from medical grade materials.

Preferably, sling portion 46, when retracting sleeve 40 is in the deployed position, forms an open loop (i.e., cradling area 47) which easily entraps organ 200 for retraction. Sling portion 46 preferably has a generally flat shape when laid open, but may be shaped differently depending upon a particular purpose, e.g., for lifting specific organs. For example, sling portion 46 may have a concave or trough-like configuration (see FIG. 2), a conical shape or a loop-like shape to fit the approximate dimensions of a particular organ. As can be appreciated, the different geometric configurations of sling portion 46 create a more uniform surface for capturing and retracting organs 200 therein. In certain embodiments, the width of the sling portion varies along its length.

The sling portion 46 is desirably manipulated by withdrawing or advancing one or more of the spindles through the shaft 20. Advancement of one or both of the spindles loosens the sling portion, allowing the surgeon to loop the sling portion around the organ to be retracted or supported. After engaging the organ in the sling portion, one or both of the spindles are withdrawn through the shaft 20, closing the sling portion around the organ.

As seen in FIG. 1, control portion 60 may include a locking mechanism 65, e.g., cam lock, suture lock, or any known mechanism, for maintaining sling portion 46 in a desired position during retraction. In certain embodiments, the locking mechanism 65 comprises a rotatable latch for frictionally engaging and securing one or more of the spindles 42, 44. In other embodiments, the locking mechanism 65 cooperates with a housing at the control portion and includes a deformable member for engaging one or more of the spindles. The deformable member is desirably arranged with a cam on the housing for urging the deformable member inwardly. A slide portion accessible to the surgeon may be connected to the deformable member for sliding the deformable member with respect to the cam on the housing. When the slide portion is advanced in one of a distal or proximal direction, the deformable member deforms inwardly, frictionally engaging and securing the spindle or spindles. In a further embodiment, the locking mechanism 65 comprises a slider having a one or more secure positions with respect to a housing at the proximal end of the shaft 20. In a further embodiment, the spindles may be tied to a cleat at the proximal end of the shaft 20, so as to secure the positions of the spindles.

In certain embodiments, a retracting force, applied to retracting sleeve 40 for withdrawing retracting sleeve 40 through tubular shaft 20, may be manually sensed by the surgeon during the manipulation of organ 200 or, in the alternative, control portion 60 may include one or more sensors configured and adapted to detect the amount of retracting force being applied to retracting sleeve 40, having organ 200 in sling portion 46, to retract retracting sleeve 40 through tubular shaft 20. In other embodiments, the sling portion may include sensors for sensing the force applied to the organ and/or detecting a loss of grip on the organ.

Sling portion 46 of retracting sleeve 40 may also include a friction enhancing texture or ribbing 62 provided along an inner surface (i.e., a tissue contacting surface) thereof to enhance a gripping force and/or degree of friction between sling portion 46 and organ 200 during manipulation thereof. In certain embodiments, the sling portion 46 of retracting sleeve 40 can be provided with a plurality of suction ports 64 formed throughout the inner surface (i.e., tissue contacting surface) thereof. Accordingly, when a vacuum is applied to suction ports 64, sling portion 46 at least partially adheres itself to organ 200 thereby enhancing the surgeons ability to handle and/or manipulate organ 200 during retraction. Desirably, each suction port 64 is in fluid communication with a source of vacuum 67 provided in control portion 60 (see FIG. 1) via a network of lumens (not shown) extending between suction ports 64 and source of vacuum 67. It is contemplated that the network of lumens are configured and dimensioned to extend through at least one of spindles 42 and 44.

In use, retractor 10 is moveable from a first position wherein spindles 42 and 44 of retracting sleeve 40 are disposed substantially entirely within tubular shaft 20 to a second position in which sling portion 46 is in an open or deployed position. More particularly, the surgeon uses control unit 60 to manipulate spindles 42, 44 and to move (i.e., open/close) sling portion 46 under organ 200. With organ 200 disposed in sling portion 46, spindles 42, 44 are withdrawn into shaft 20 to envelope, capture and retract organ 200. Preferably, the surgeon can sense the amount of pressure being applied to organ 200 during retraction. Locking mechanism 65 is then desirably actuated to fix the position of spindles 42, 44 and to fix organ 200 in the retracted position.

Upon completion of the surgical procedure, or any part thereof, locking mechanism 65 is released and organ 200 is allowed to return to its natural, pre-retracted, position. Retractor 10 is then withdrawn through the trocar assembly.

Figure 4A:
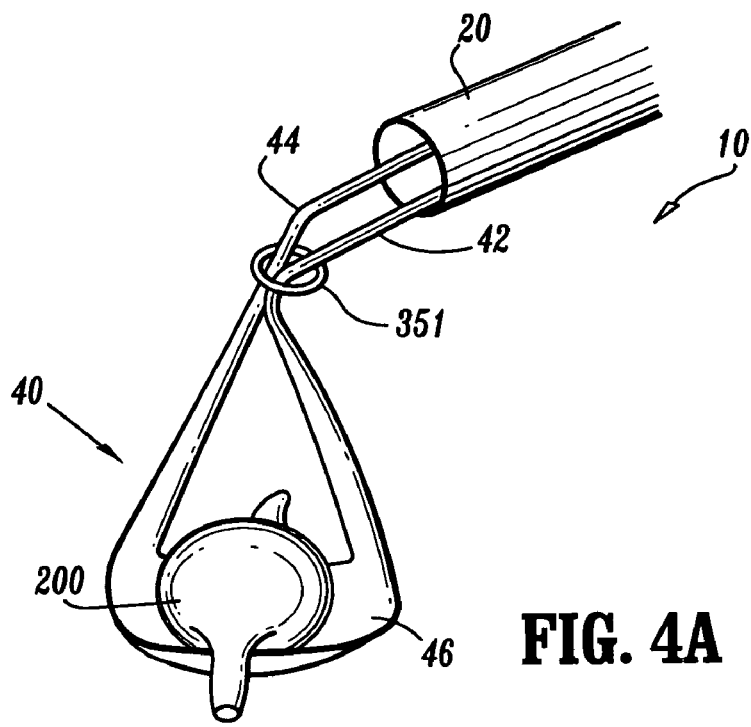
FIG. 4A is a perspective view of an endoscopic retractor apparatus in accordance with a further embodiment of the invention.

A further embodiment of the invention is shown in FIG. 4A. A cinch for retractor 10 is shown generally as 351. Cinch 351 is configured and adapted to surround at least a portion of spindles 42, 44 and of sling portion 46. It is envisioned that cinch 351 is a loop-like structure, preferably a rigid annular ring, to facilitate positioning of cinch 351 along spindles 42, 44, preferably made from steel, plastic or the like. In use, cinch 351 is distally advanced beyond the distal ends of spindles 42, 44 and down over sling portion 46 in order to remotely close and/or constrict sling portion 46 around organs/tissue disposed therein. The cinch 351 may be attached to the shaft 20, or to one or more of the spindles 42, 44, or may be unattached.

Figure 4B:
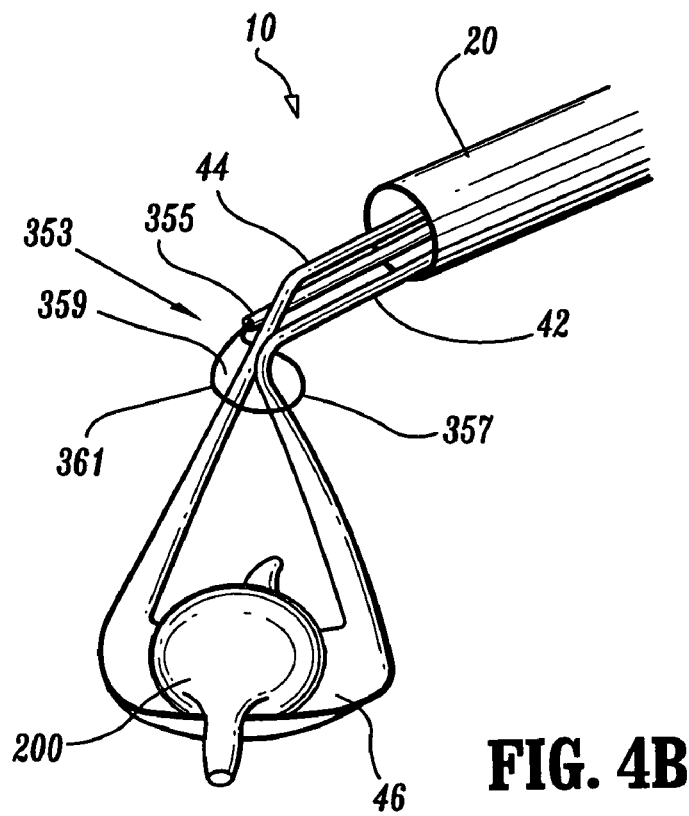
FIG. 4B is a perspective view of an endoscopic retractor apparatus in accordance with another embodiment.

In another embodiment of the invention as shown in FIG. 4B, a cinching mechanism for retractor 10 is shown generally as 353. Cinching mechanism 353 is configured and adapted to surround at least a portion of spindles 42, 44 and of sling portion 46. Cinching mechanism 353 includes an elongate tubular body 355, translatably received in a lumen of retracting sleeve 40, and an adjustable loop 357 extending from tubular body 355 and defining an opening 359. It is contemplated that loop 357 is made from sutures and/or wires 361. Accordingly, opening 359 of loop 357 can be enlarged by releasing and/or feeding more wire 361 from tubular body 355 and constricted by withdrawing wire 361 into tubular body 355. In use, with organ/tissue 200 disposed in sling portion 46 and with wire 361 disposed around sling portion 46, wire 361 of loop 357 is withdrawn (i.e., to constrict opening 359 of loop 357), preferably around a region of sling portion 46 between organ 200 and the distal end of spindles 42, 44, so that sling portion 46 is closed and/or cinched around organ 200. Loop 357 of cinching mechanism 353 can be placed into position around sling portion 46, between organ 200 and the distal end of spindles 42, 44, either before or after organ 200 is placed in sling portion 46. Cinching mechanism 353 can be operatively connected to control portion 60 such that cinching mechanism 353 can be remotely operated by the surgeon.

Figure 5A:
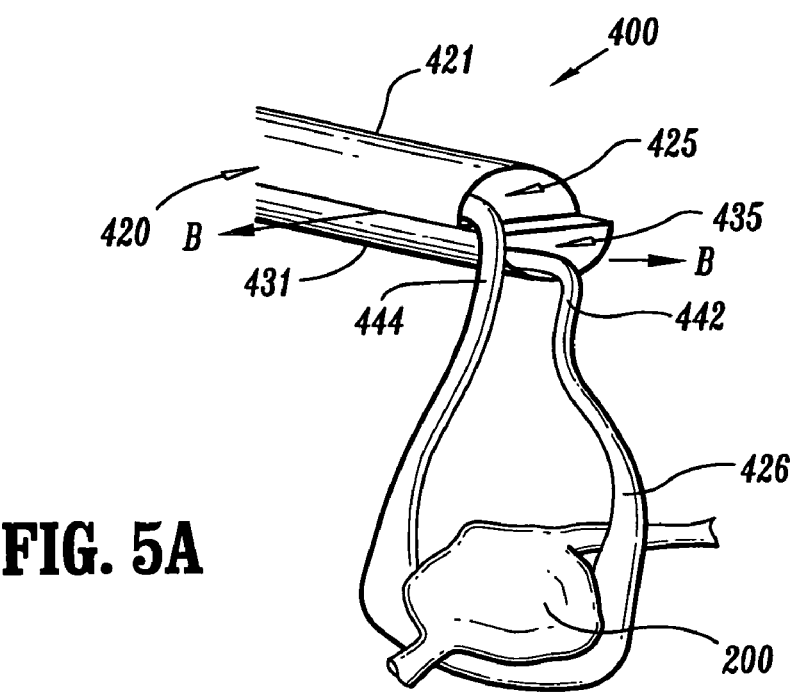
FIG. 5A is a perspective view of an endoscopic retractor apparatus in accordance with another embodiment of the present invention.
Figure 5B:
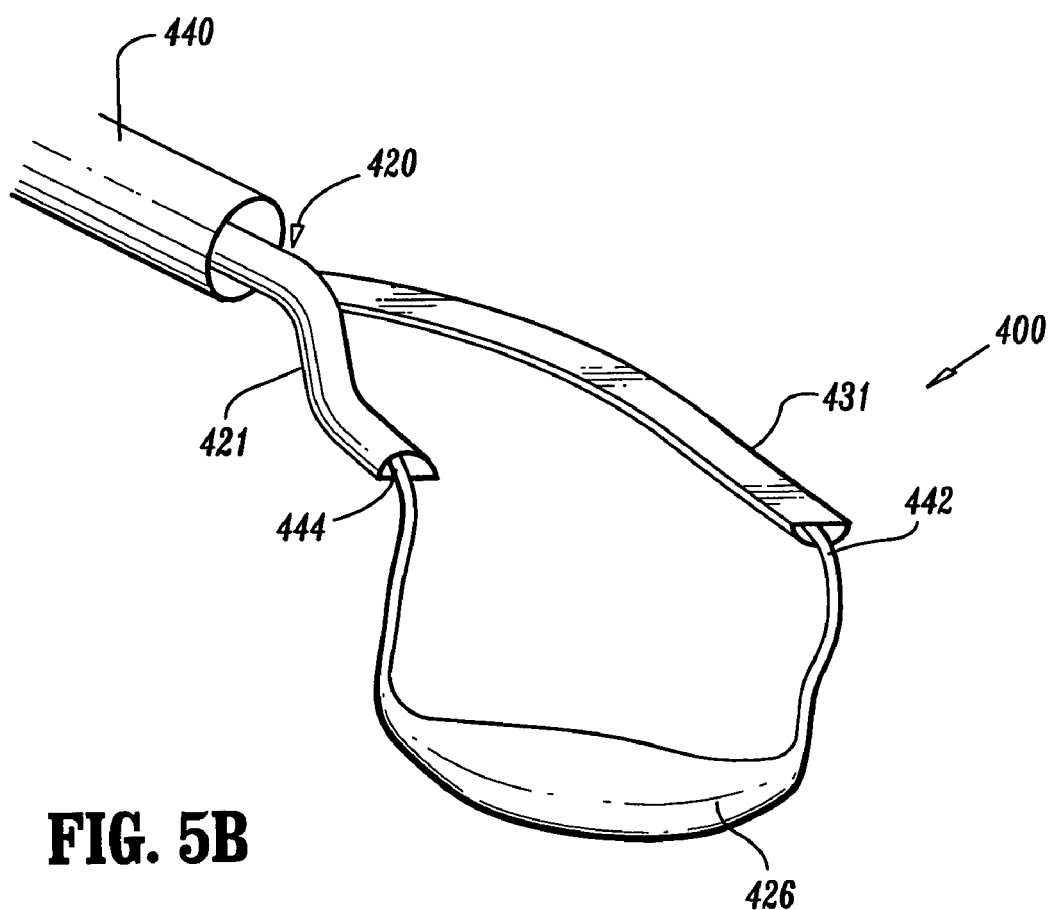
FIG. 5B is a perspective view of an endoscopic retractor apparatus in accordance with the embodiment of FIG. 5A.

In a further embodiment of the invention, as shown in FIGS. 5A and 5B, an endoscopic retractor apparatus is generally shown as 400. Retractor 400 includes a tubular shaft 420 having a first section 421 and a second section 431. In certain embodiments, each of first section 421 and second section 431 are substantially semicircular in shape such that when first section 421 and second section 431 are in vertical registration with one another, first and second sections 421, 431 have a substantially circular cross-sectional profile. Each section 421, 431 includes a lumen 425, 435, respectively, extending therethrough. Retractor 400 further includes a retracting sleeve 440 having a first and a second spindle 442, 444 disposed, one each, in respective first and second sections 421, 431 and a sling portion 426 extending between the distal ends of spindles 442, 444. Preferably, sections 421, 431 and spindles 442, 444 can be remotely operated by the surgeon.

Tubular shaft 420 has a first position in which first and second sections 421, 431 are in vertical registration with one another (see FIG. 5A) and a plurality of second positions in which first and second sections 421, 431 are out of vertical registration with one another (see FIG. 5B). Preferably, the distal ends of first and second sections 421, 431 can be moved relative to one another, in the direction indicated by arrows "B", to separate and approximate first and second sections 421, 431 relative to one another to each of the first and the second positions. It is envisioned that having separate movable first and second sections 421, 431 increases the mechanical ability of sling portion 426 by allowing first and second sections 421, 431 and, in turn, spindles 442, 444, to move relative to one another, thus facilitating manipulation of organ 200.

In certain embodiments, each section 421, 431 of tubular shaft 420 is fabricated from a shape memory material, such as, for example, the shape memory alloy NITANOL. In this manner, sections 421, 431 can be fabricated to have a first configuration in which sections 421, 431 are in longitudinal registration with one another and a second configuration, when exposed to the body cavity, in which sections 421, 431 are deployed to be transversely spaced from one another. In order to return the distal end of sections 421, 431 to the first configuration, a sleeve or cannula 440 can be slidingly provided around the proximal end of sections 421, 431. In this manner, by holding sleeve 440 stationary, withdrawal of sections 421, 431 through sleeve 440 causes the distal end of sections 421, 431 to be urged from the second configuration to the first configuration. In certain embodiments, the first section 421 and second section 431 are biased in the second configuration. The apparatus may include biasing structure between the first section 421 and second section 431 or the first section 421 and second section 431 may be made from a material that is biased in the second configuration.

In operation, with first and second sections 421, 431 in vertical registration with one another (i.e., tubular shaft 420 having a low profile), tubular shaft 420 is inserted into the operative site, sleeve 420 is deployed by extending spindles 442, 444 distally out of lumens 425, 435 of first and second sections 421, 431, and the distal ends of first and second sections 421, 431 are moved in direction "B" to thereby deploy and/or open sling portion 426. Once organ 200 is placed in sling portion 426, the distal ends of first and second half-sections 421, 431 are approximated toward one another to thereby envelope organ 200 in sling portion 426.

Preferably, tubular shaft 420 is inserted into the body cavity such that the pivot point between first and second sections 421, 431 is as close to the entrance to the body cavity as possible. In this manner, the distal end of first and second sections 421, 431 are given the greatest range of motion with a minimum amount of stress caused to the entrance of the body cavity.

Alternatively, sections 421, 431 of tubular shaft 420 are fabricated from a shape memory alloy, with sleeve or cannula 440 inserted into the body cavity and the distal ends of sections 421, 431 of tubular shaft 420 in the first configuration, tubular shaft 420 is inserted into the body cavity through sleeve 440 such that the distal end of sections 421, 431 are exposed to the body cavity to thereby deploy the distal ends of sections 421, 431 to the second configuration. Upon completion of the surgical procedure, tubular shaft 420 is withdrawn through sleeve 440 thereby urging the distal ends of section 421, 431 from the second configuration to the first configuration.

Although the illustrative embodiments of the present disclosure have been described herein, it is to be understood that the disclosure is not limited to those precise embodiments, and that various other changes and modifications may be affected therein by one skilled in the art without departing from the scope or spirit of the disclosure. All such changes and modifications are intended to be included within the scope of the disclosure.

What is claimed is:

1. An endoscopic retractor apparatus for retracting an organ during minimally invasive surgery, comprising:
   an elongate shaft having proximal and distal ends and a lumen extending therebetween; and
   a retracting sleeve operatively associated with the elongate shaft, the retracting sleeve including:
   a first and a second spindle each disposable in the lumen of the elongated shaft, each spindle being selectively independently translatable through at least a portion of the lumen of the elongate shaft; and
   a sling portion extending between the distal ends of the first and second spindles, the sling portion defining a cradle for supporting organs therein, the sling portion being selectively movable upon translation of at least one of the first and second spindles.

2. The endoscopic retractor apparatus according to claim 1, further comprising a control portion operatively connected to a proximal end of each of the shaft, the first spindle and the second spindle, the control portion cooperating with the first and the second spindles to allow a user to remotely move the sling portion to engage the organs.

3. The endoscopic retractor apparatus according to claim 2, wherein the control portion includes a locking mechanism for maintaining the sling portion in a desired position relative to the retracting sleeve.

4. The endoscopic retractor apparatus according to claim 3, wherein the locking mechanism maintains the sling portion in at least one of a deployed and a retracted position.

5. The endoscopic retractor apparatus according to claim 1, wherein the apparatus includes a first position in which the sling portion of the retracting sleeve is at least partially retained in the lumen of the elongate shaft and a second position in which the sling portion of the retracting sleeve is not retained in the lumen of the elongated shaft.

6. The endoscopic retractor apparatus according to claim 5, wherein when the endoscopic retractor apparatus is in the second position the sling portion defines a cradling area for engaging the organs.

7. The endoscopic retractor apparatus according to claim 1, wherein the sling portion is fabricated from one of a mesh, ribbon and cloth.

8. The endoscopic retractor apparatus according to claim 1, wherein the sling portion includes ribbing provided along a tissue contacting surface thereof for enhancing a gripping force between the sling portion and the organs.

9. The endoscopic retractor apparatus according to claim 1, wherein the sling portion includes a plurality of ports formed along a tissue contacting surface thereof.

10. The endoscopic retractor apparatus according to claim 9, wherein the sling portion is operatively connected to a control portion, wherein the control portion is configured and adapted to deliver vacuum to at least a portion of the plurality of ports formed in the sling portion.

11. The endoscopic retractor apparatus according to claim 10, wherein the vacuum is delivered to the portion of the plurality of ports through at least one of the first and second spindles.

12. The endoscopic retractor apparatus according to claim 1, further comprising a cinch configured and adapted to constrict at least a portion of the sling portion about the organs.

13. The endoscopic retractor apparatus according to claim 12, wherein the cinch is a substantially rigid annular structure.

14. The endoscopic retractor apparatus according to claim 13, wherein the cinch is disposed about the first and the second spindle.

15. The endoscopic retractor apparatus according to claim 14, wherein as the cinch is displaced in a direction to space the cinch from the distal end of the first and the second spindles, the sling portion is constricted.

16. The endoscopic retractor apparatus according to claim 1, further including a cinching mechanism configured and adapted to constrict at least a portion of the sling portion about the organs.

17. The endoscopic retractor apparatus according to claim 16, wherein cinching mechanism includes:
 an elongate tubular body translatably received in the lumen of the elongate shaft; and
 a loop extending from a distal end of the elongate tubular body, the loop defining an opening, wherein the opening of the loop can be enlarged by releasing loop from the tubular body and the opening of the loop can be reduced by withdrawing loop into the tubular body.

18. The endoscopic retractor apparatus according to claim 17, wherein the loop is fabricated from at least one of sutures and wires.

19. The endoscopic retractor apparatus according to claim 18, wherein when the loop of the cinching mechanism is positioned between the sling portion and the distal ends of the spindles, when the organs are contained within the sling portion, withdrawal of loop into tubular body causes the sling portion to constrict around the organs.

20. The apparatus of claim 1, wherein the first spindle and the second spindle are integrally formed with the sling portion.

21. An endoscopic retractor apparatus for retracting and/or positioning organs during minimally invasive surgery, comprising:
 an elongate shaft having a first section defining a lumen extending therethrough and a second section defining a lumen extending therethrough;
 a first spindle disposable in the lumen of the first section and selectively independently translatable through at least a portion of the lumen of the first section; and
 a second spindle disposable in the lumen of the second section and selectively independently translatable through at least a portion of the lumen of the second section.

22. The endoscopic retractor apparatus according to claim 21, wherein the first and second sections of the elongate shaft have a first position in which the first and second section are in vertical registration with one another and a second position in which the first and second sections are out of vertical alignment with one another.

23. The endoscopic retractor apparatus according to claim 22, wherein when the first and second sections are moved from the first position to the second position, the sling portion is opened, and when the first and second sections are moved from the second position to the first position, the sling portion is closed.

24. The endoscopic retractor apparatus according to claim 21, wherein each of the first and second sections are fabricated from a shape memory alloy.

25. The endoscopic retractor apparatus according to claim 24, wherein the elongate shaft has a first configuration in which distal ends of the first and second sections are in vertical registration with one another and a second configuration in which the distal ends of the first and second sections are transversely separated from one another upon introduction to a body cavity.

26. The endoscopic retractor apparatus according to claim 25, further including a sleeve disposable about the elongate shaft, wherein the elongate shaft is urged from the second configuration to the first configuration upon withdrawal of the elongate shaft through the sleeve.

* * * * *